United States Patent [19]

Arnaud et al.

[11] Patent Number: 5,080,823
[45] Date of Patent: Jan. 14, 1992

[54] AZEOTROPIC MIXTURE WITH 1,1,1-TRIFLUOROETHANE AND PROPANE A LOW BOILING POINT AND ITS APPLICATONS AS A REFRIGERANT FLUID, AS AN AEROSOL PROPELLANT, OR AS A BLOWING AGENT FOR PLASTIC FOAMS

[75] Inventors: Didier Arnaud, Courbevoie; Jean C. Tanguy, Sannios, both of France

[73] Assignee: Societe Atochem, Puteaux, France

[21] Appl. No.: 679,407

[22] Filed: Apr. 2, 1991

[30] Foreign Application Priority Data

Apr. 2, 1990 [FR] France ................ 90 04168

[51] Int. Cl.$^5$ ................ C11D 7/50; C08J 9/14; C09K 3/30; C09K 5/04
[52] U.S. Cl. ................ 252/;172; 62/114; 203/67; 252/67; 252/162; 252/305; 252/364; 252/DIG. 9; 264/53; 264/DIG. 5; 521/98; 521/131
[58] Field of Search ........ 252/67, 162, 170, 171, 252/172, 305, 364, DIG. 9; 203/67; 62/114; 264/53, DIG. 5; 521/98, 131

[56] References Cited

U.S. PATENT DOCUMENTS

| | | | |
|---|---|---|---|
| 2,511,993 | 6/1950 | Reed | 252/67 |
| 4,085,073 | 4/1978 | Suh et al. | 264/DIG. 5 |
| 4,198,313 | 4/1980 | Bargigia | 252/305 |
| 4,482,465 | 11/1984 | Gray | 252/67 |

FOREIGN PATENT DOCUMENTS 63-105088  5/1988  Japan .

OTHER PUBLICATIONS

*Research Disclosure* vol. 162, Oct. 1977 disclosure # 16265 "Fluorocarbon Azeotropes" by E. I. du Pont de Nemours & Co., Inc. p. 70.

*Primary Examiner*—Paul Lieberman
*Assistant Examiner*—Linda D. Skaling
*Attorney, Agent, or Firm*—Morgan & Finnegan

[57] ABSTRACT

The invention relates to an azeotrope with a minimum boiling point, capable of being employed as a refrigerating fluid replacing trifluorobromomethane (Halon 1301) in industrial refrigeration systems at very low temperature with single-stage compression.

The azeotrope according to the invention is a mixture of 1,1,1-trifluoroethane (HFA 143a) and of propane (R290). At the normal boiling point (approximately $-53.4°$ C. at 1.013 bars), its 1,1,1-trifluoroethane content is approximately 70.6 mass % and that of propane 29.4 %.

This azeotrope can also be employed as an aerosol propellant or as a blowing agent for plastic foams.

4 Claims, 1 Drawing Sheet

AZEOTROPIC MIXTURE WITH 1,1,1-TRIFLUOROETHANE AND PROPANE A LOW BOILING POINT AND ITS APPLICATONS AS A REFRIGERANT FLUID, AS AN AEROSOL PROPELLANT, OR AS A BLOWING AGENT FOR PLASTIC FOAMS

FIELD OF THE INVENTION

The present invention relates to a mixture of refrigerant fluids of low boiling point, which have no effect on stratospheric ozone and which can be employed to replace trifluorobromomethane in industrial refrigeration systems at very low temperature with single-stage compression.

BACKGROUND OF THE INVENTION

It has now been established that, because of its high coefficient of action on ozone, trifluorobromomethane (Halon 1301) will have to be replaced, in the shorter or longer term, by refrigerant fluids containing neither chlorine nor bromine and, consequently, having no effect on stratospheric ozone.

Bearing in mind its very low action on the environment, 1,1,1-trifluoroethane (HFA 143a) has already been proposed as a substitute for the CFCs. However, because of its boiling point ($-47.6°$ C.), the use of HFA 143a by itself is restricted to applications with evaporation temperatures near $-45°$ C. and cannot be envisaged for applications with very low boiling temperatures (for example $-60°$ C. to $-50°$ C.).

In fact, the minimum temperature reached in the evaporator is in practice limited by the value of the normal boiling temperature of the refrigerant fluid in order to avoid the entry of air or of brine into the plant in the case of evaporator leakages, which would present the risk of interfering with the normal operation of the system.

DESCRIPTION OF THE INVENTION

It has now been found that 1,1,1-trifluoroethane (HFA 143a) and propane (R290) form an azeotrope with a minimum boiling point equal to approximately $-53.4°$ C. at 1.013 bars and whose R290 content at the normal boiling point is approximately 29.4 mass%. Of course, this composition varies as a function of the pressure of the mixture and, at a given pressure, can be easily determined by following well-known methods.

Because of its very low boiling point the azeotropic mixture according to the invention can be employed as a refrigerant fluid in industrial single-stage applications with low boiling temperatures ($-50°$ C.) as in the case of deep-freezing tunnels where pure R290 and HFA 143a cannot be used because of their boiling points being too high.

Given its physical properties which are closely related to those of the CFCs, the mixture according to the invention can also be employed as an aerosol propellant or as a blowing agent for plastic foams.

BRIEF DESCRIPTION OF THE DRAWINGS

The FIGURE shows the liquid/vapor equilibrium curve for HFA 143a/R290.

EXAMPLES

Figure 1:
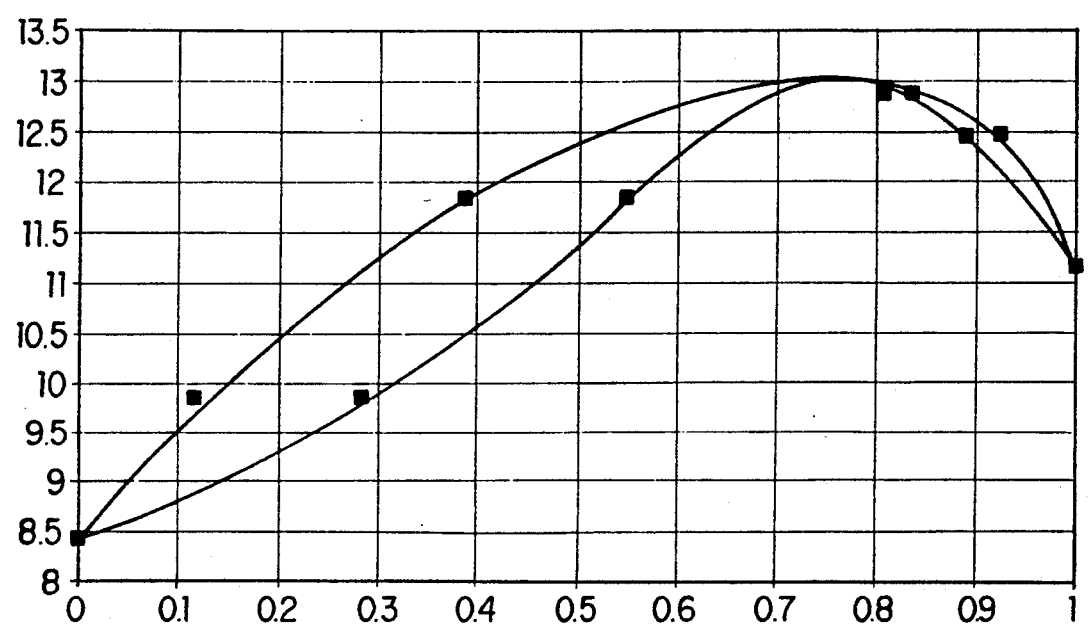

The following examples illustrate the invention without limiting it.

EXAMPLE 1

The azeotrope according to the invention was studied experimentally at various temperatures by analysis, by using gas phase chromatography, of the compositions of the liquid phase and of the vapor phase for different mixtures of HFA 143a and R290.

Pressures were measured with an accuracy better than 0.02 bars by means of a Heise manometer. Temperatures were measured to within $0.02°$ C. by means of a 1000-ohm platinum probe.

The FIGURE shows the liquid/vapor equilibrium curve for HFA 143a/R290 mixtures, established at a temperature of $20.1°$ C. In this FIGURE or graph, the abscissa axis shows the mass fraction of HFA 143a and the ordinate axis the absolute pressure in bars; the black squares correspond to the experimental points.

A curve similar to that of the FIGURE is obtained for each temperature. On successive additions of HFA 143a to R290 the pressure developed by the mixture increases regularly, then passes through a maximum and decreases regularly, which demonstrates the existence of the minimum boiling point azeotrope.

The correlation of the experimental points obtained in this way for several isotherms was obtained using well-known techniques, by means of a data-processing simulation.

The normal boiling points thus determined for various HFA 143a compositions are summarized in the following Table 1:

TABLE 1

| Composition, mass % of HFA 143a | Normal boiling point °C. |
| --- | --- |
| 100 | −46.7 |
| 90 | −52.3 |
| 80 | −53.3 |
| 70.6 | −53.4 |
| 70 | −53.3 |
| 60 | −53.2 |
| 50 | −53.1 |
| 40 | −52.7 |
| 30 | −51.7 |
| 20 | −49.9 |
| 10 | −46.7 |
| 0 | −41.5 |

The results of these correlations demonstrate the normal boiling point minimum in the case of a mass fraction of HFA 143a equal to 70.6%, and this enables the azeotrope to be characterized by:

its normal boiling point, which is equal to approximately $-53.4°$ C.

its mass composition, equal to approximately 70.6% of HFA 143a.

Table 2, which follows, gives the pressure/temperature relationship for this azeotrope, compared with that of the pure substances.

TABLE 2

| | Absolute Pressure (bar) | | |
| --- | --- | --- | --- |
| Temperature (°C.) | R290/HFA 143a azeotrope | pure HFA 143a | pure R290 |
| −50.0 | 1.19 | 0.90 | 0.68 |
| −20.0 | 3.93 | 3.22 | 2.43 |
| −0.2 | 7.40 | 6.19 | 4.71 |
| +20.1 | 12.9 | 11.2 | 8.41 |
| +50.0 | 25.8 | 23.1 | 17.0 |

The vapor pressure of the azeotrope remains greater than the vapor pressure of the pure substances over a wide temperature range. These data show that the mixture remains azeotropic throughout this temperature interval.

EXAMPLE 2

This example illustrates the use of the azeotrope according to the invention as a refrigerant fluid.

The thermodynamic performances of the azeotropic mixture according to the invention were compared with the performances of the two constituents by themselves, in conditions closely related to those encountered in single-stage deep-freezing tunnels, namely the following:

| | |
|---|---|
| condensation temperature | +30° C. |
| evaporation temperature | −50° C. |
| liquid supercooling | +5° C. |
| vapor superheating at the compressor suction | +20° C. |

Table 3 summarizes the thermodynamic performances observed in these conditions for pure HFA 143a, pure R290 and the azeotropic mixture according to the invention.

TABLE 3

| | R290/HFA 143a Azeotrope | Pure HFA 143a | Pure R290 |
|---|---|---|---|
| Evaporation pressure (bar) | 1.19 | 0.90 | 0.68 |
| Condensation pressure (bar) | 16.5 | 14.4 | 10.9 |
| Discharge temperature (°C.) | 64.1 | 68.4 | 69.3 |
| Compression ratio | 13.9 | 16.0 | 15.9 |
| Refrigeration capacity (kJ/m³) | 623.6 | 527.1 | 428.5 |
| Coefficient of performance | 1.78 | 1.86 | 1.97 |

It can be seen that the azeotropic mixture according to the invention offers a certain number of advantages over HFA 143a or R290 in the pure state, especially:

- a lower discharge temperature ensuring a longer working life of the compressor
- a lower compression ratio and therefore an improvement in the volumetric efficiency of the compressor and consequently lower running costs of the plant
- a considerably greater available volumetric refrigeration capacity which, in practice, for a given refrigeration capacity, makes it possible to employ a smaller compressor than that defined for employing HFA 143a or R290 in pure form.

This increase in the available volumetric refrigeration capacity for the azeotrope according to the invention also makes it possible to increase by 18% the available refrigeration capacity of an already existing plant defined for HFA 143a.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Minimum boiling point azeotrope consisting of a mixture of about 50 to 80 mass% 1,1,1-trifluoroethane and the balance propane, propane and at its normal boiling point of approximately 70.6 mass% of 1,1,1-trifluoroethane and containing approximately 70.6 mass% of 1,1,1-trifluoroethane and 29.4 mass% of propane.

2. A method of refrigeration comprising condensing and evaporating the azeotrope of claim 1.

3. A method of preparing an aerosol wherein the propellant is the azeotrope of claim 1.

4. A method of manufacturing plastic foams wherein the blowing agent is the azeotrope of claim 1.

* * * * *